United States Patent [19]

Franklin

[11] 4,385,059

[45] May 24, 1983

[54] THIAZOLE COMPOSITIONS

[75] Inventor: Richard A. Franklin, Reading, England

[73] Assignee: John Wyeth and Brother Limited, Maidenhead, England

[21] Appl. No.: 247,460

[22] Filed: Mar. 25, 1981

[30] Foreign Application Priority Data

Apr. 3, 1980 [GB] United Kingdom ............... 8011251
Apr. 26, 1980 [GB] United Kingdom ............... 8013860

[51] Int. Cl.³ .................. C07D 277/20; A61K 31/425
[52] U.S. Cl. ..................................... 424/270; 548/202; 548/203
[58] Field of Search ................ 548/203, 202; 424/270

[56] References Cited

FOREIGN PATENT DOCUMENTS 1145884 3/1969 United Kingdom .

OTHER PUBLICATIONS

J. Med. Chem. (1974) vol. 17, pp. 1177–1188.
Boll Chim Farm 117, 19–26 (1978).

Primary Examiner—Nicholas S. Rizzo
Attorney, Agent, or Firm—Richard K. Jackson

[57] ABSTRACT

The invention concerns compounds of formula

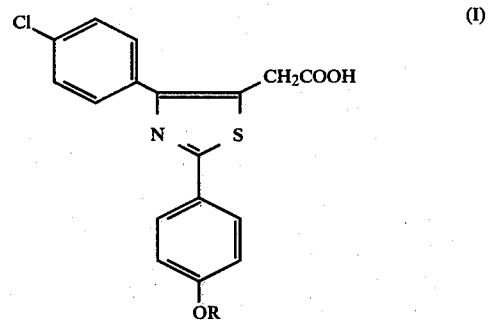

or salts thereof, wherein R represents hydrogen which possess anti-inflammatory activity and have low toxicity. Methods for preparing the compounds and pharmaceutical compositions are also disclosed.

2 Claims, No Drawings

THIAZOLE COMPOSITIONS

This invention relates to a novel thiazole possessing pharmaceutical activity to pharmaceutical compositions containing said thiazole and to method of preparing the thiazole.

In UK Patent Specification No. 1,145,884 there are described and claimed compounds of the general formula (A)

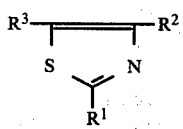

and acid addition salts thereof, in which $R^1$ and $R^2$ are the same or different and are substituted aryl radicals (which may be heteroaryl radicals) and $R^3$ is a lower aliphatic carboxylic acid radical containing from 2 to 6 carbon atoms or a salt, ester, amide, nitrile or hydroxamic acid derivative thereof, said radical $R^3$ being attached to the thiazole ring by a carbon atom on the aliphatic chain.

According to UK Patent Specification No. 1,145,884 the compounds of formula A possess pharmacological activity particularly anti-inflammatory activity. Examples of $R^1$ and $R^2$ are unsubstituted phenyl and phenyl substituted by halogen, lower alkyl, lower alkoxy, nitro, amino, substituted amino, mercapto, alkythio, alkylsulphonyl, or trihalomethyl.

The anti-inflammatory activity of specific compounds of formula A against carrageenin-induced edema in the rat hind paw was extensively reported by Brown et al, in *Journal of Medicinal Chemistry*, 1974, Vol. 17 no. 11, pps. 1177 to 1181. Structure activity relationship revealed that the anti-inflammatory activity was found to be optimised when $R^2$ was 4-chlorophenyl. However, the preferred $R^1$ group was found to be phenyl and 4-substitution of this ring reduced the anti-inflammatory activity. Thus 4-methoxy and 4-carboxy substitution both substantially reduced activity when $R^2$ was 4-chlorophenyl.

I have now surprisingly found that a thiazole-5-acetic acid not specifically mentioned in the general formula (A) wherein $R^1$ represents phenyl having a 4-hydroxy substituent possesses marked anti-inflammatory activity, especially when administered topically. Furthermore this compound, 4-(4-chlorophenyl)-2-(4-hydroxyphenyl)thiazole-5-acetic acid, possesses very low toxicity and accordingly has a higher therapeutic index than the hitherto preferred compound: 4-(4-chlorophenyl)-2-phenylthiazole-5-acetic acid (fentiazac).

Accordingly this invention provides a compound having the formula:

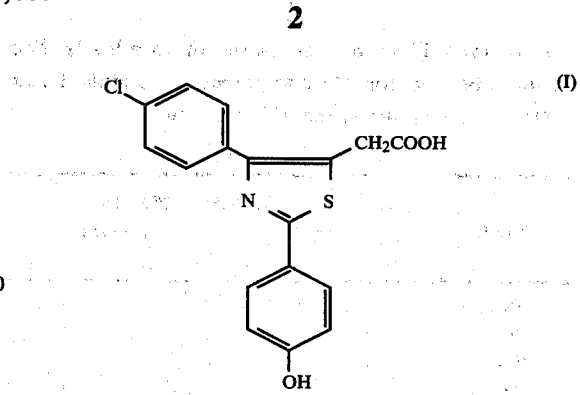

and salts thereof.

The compound of formula I forms salts, for example acid addition salts with acids such as hydrochloric and hydrobromic acid, or alkali metal (e.g. sodium or potassium) or alkaline earth metal (e.g. calcium) salts. Such salts may be prepared in known manner.

The compound of formula I was tested for anti-inflammatory activity by the following procedure based on Tonelli et al, *Endocrinology* 77, 625 (1965):

Sprague-Dawley female rats, weighing 60 to 70 grams, are used in groups of 10. Ear edema is induced by inuncting both sides of the ear with an irritant mixture. This mixture containing 1% croton oil, 20% pyridine, 5% water and 74% diethyl ether, with or without test compound, is applied only once and only to the right ear. Six hours later the animals are sacrificed; a 9 mm diameter portion of both ears is punched out with a cork borer and weighed. The anti-inflammatory activity of the test agent is assessed by expressing the percent of the difference in average weight increase between the ears of the control groups and of the treated group.

$$\% \text{ Inhibition} = 100 \times \frac{\left(\begin{array}{c}\text{Avg. inc. in wt. of}\\ \text{test groups}\end{array}\right) - \left(\begin{array}{c}\text{avg. inc. in wt. of}\\ \text{controls}\end{array}\right)}{\left(\begin{array}{c}\text{Avg. inc. in wt. of}\\ \text{controls}\end{array}\right)}$$

Results found for 4-(Chlorophenyl)-2-(4-hydroxyphenyl)-thiazole-5-acetic acid are tabulated below, together with results found in 3 tests for the preferred compound reported by Brown et al in J.Med.Chem.-(loc-cit) namely: 4-(p-chlorophenyl)-2-phenylthiazole-5-acetic acid (fentiazac).

| Compound | Dose | % Inhibition | | |
|---|---|---|---|---|
| 4-(Chlorophenyl)-2- | 50 μg | 16% | | |
| (4-hydroxyphenyl)- | 500 μg | 33% | | |
| thiazole-5-acetic acid | 2.5 mg | 86% | | |
| | 5 mg | 92% | | |
| fentiazac | 50 μg | −30, | 15, | −7% |
| | 500 μg | 10, | 35, | 52% |
| | 2.5 mg | 93, | 79, | 89% |
| | 5 mg | 92, | 93, | 93% |

The compounds both show marked anti-inflammatory activity of about the same order.

Toxicity of the compound of formula I was measured by administering orally to groups of 3 male and 3 female nonβstarved TFW mice at a series of dose levels. The results obtained for the compound of formula I and fentiazac are shown in the Table below:

| Dose level | No. Dead (hours from dosing) | | | |
|---|---|---|---|---|
| | Formula I | | Fentiazac | |
| mg/kg | 24 hours | 7 days | 24 hours | 7 days |
| 450 | 0 | 0 | 2 | 3 |
| 675 | 1 | 1 | 3 | 6 |
| 1012.5 | 1 | 1 | 3 | 6 |
| 1518.8 | 1 | 1 | 2 | 4 |
| 2278.1 | 0 | 0 | 3 | 3 |
| 3417.2 | 0 | 0 | 5 | 6 |

The compound 4-(p-chlorophenyl)-2-(p-hydroxyphenyl)-thiazole-5-acetic acid was found to be considerably less toxic than fentiazac.

This invention also provides processes for preparing the compound of formula I. Such processes are outlined in U.K. Patent Specification Nos. 1,145,884 and 1,262,292. Accordingly this invention provides a process for preparing a compound of formula I or an acid addition salt thereof which comprises (a) reacting an α-haloketone of general formula:

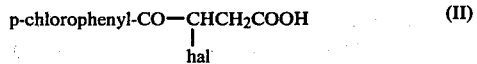

wherein hal is a halogen atom, with a thioamide of general formula:

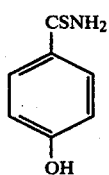

or (b) dehydrating a compound of formula

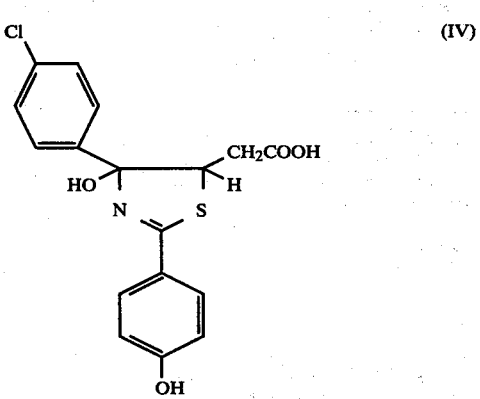

(c) dealkylating a compound of formula:

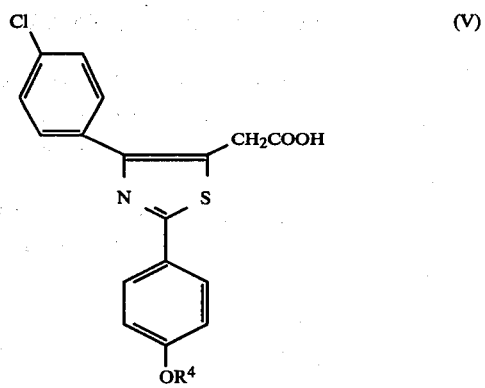

wherein $R^4$ is alkyl or aralkyl, or (d) hydrolysing a mono- or di-ester of formula:

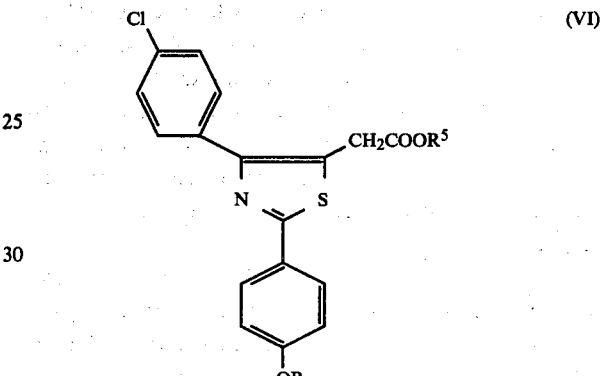

wherein R is H or an acyl group and $R^5$ is H or an alkyl or aralkyl group with the proviso that R and $R^5$ are not both hydrogen.

Methods for carrying out processes (a) and (b) above are extensively described in our U.K. Patent Specification Nos. 1,145,882 and 1,262,292.

Methods for carrying out dealkylation in process step (d) are well known in the art, for example treating the ethers with hydrogen bromide, hydrogen iodide or boron tribromide. Preferably $R^4$ is alkyl of 1 to 4 carbon atoms, most preferably methyl.

Hydrolysis of compounds of formula (VI) may be carried out in known manner, e.g. using an alkali metal hydroxide and acidifying.

The invention provides a pharmaceutical composition comprising a compound of general formula (I) or a pharmaceutically acceptable salt thereof in association with a pharmaceutically acceptable carrier. Any suitable carrier known in the art can be used to prepare the pharmaceutical composition. In such a composition, the carrier is generally a solid or liquid, or a mixture of a solid and a liquid. In some aerosol compositions the carrier may be a gas.

Solid form compositions include powders, granules, tablets, capsules (e.g. hard and soft gelatin capsules), suppositaries and pessaries. A solid carrier can be, for example, one or more substances which may also act as flavouring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils and fats. The liquid carrier can contain other suitable pharmaceutical additives such as solubilizers, emulsifiers, buffers, preservatives, sweetners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glyceroland glycols) and their derivatives, and oils (e.g. fractionated coconut oil and arachis oil). For parental administration the carrier can also be an oily ester such as ethyl oleate and isopropyl myristate. Sterile liquid carriers are used in sterile liquid form compositions for parental administration. The liquid carrier for pressurised compositions can be a halogenated hydrocarbon or other pharmaceutically acceptable propellent.

Liquid pharmaceutical compositions which are sterile solutions or suspensions can be utilised by, for example, intramuscular, intraperitoneal or subcutaneous injection. Sterile solutions can also be administered intraveously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form. The quantity of the active ingredient in a unit dose of composition may be varied or adjusted from 0.5 mg. or less to 750 mg. or more, according to the particular need and the activity of the active ingredient. The invention also includes the compounds in the absence of the carrier where the compounds are in unit dosage form.

The present invention also provides a semi-solid or aerosol pharmaceutical composition for topical administration comprising a compound of formula I or a pharmaceutically acceptable salt thereof in association with a pharmaceutically acceptable topical carrier.

By a 'semi-solid pharmaceutical composition' is meant an ointment, cream, salve, paste, jelly or other pharmaceutically or cosmetic composition of substantially similar consistency suitable for application to the skin. Examples of semi-solid compositions are given in Chapter 17 of The Theory and Practice of Industrial Pharmacy, Lachman, Lieberman and Kanig, published by Lea and Febiger (1970) and in Chapter 67 of Remington's Pharmaceutical Sciences, 15th Edition (1975) published by Mack Publishing Company.

Preferably, the topical compositions of the present invention contain from about 0.1% to about 20% by weight of the active ingredient. The compositions may, for example, contain from about 0.5% (preferably from about 1%) to about 10% by weight of the active ingredient.

The carrier used in the topical compositions of the present invention may be any carrier suitable for preparing topical semi-solid compositions or topical aerosol compositions. Examples of suitable carriers for semi-solid compositions are given in Lachman, Lieberman and Kanig (loc-cit) and in Chapter 67 of Remington's Pharmaceutical Sciences, (loc-cit). The carrier for the semi-solid composition may be, for example an emulsion base of the oil in water class (e.g. an emulsion of soft and liquid paraffins in water). Alternatively, the carrier may be an absorption base (e.g. a mixture of wool fat and soft paraffin). A third class of suitable carriers are water miscible bases (e.g. mixtures of high and low molecular weight polythene glycols).

When the composition is in aerosol form for topical administration, the composition may comprise the active ingredient and an easily liquifiable gas. Examples of such liquifiable gases are halogenated hydrocarbons and liquified lower hydrocarbons, both of which are well known as propellants in the aerosol art. (By "lower hydrocarbon" is meant a hydrocarbon containing up to six carbon atoms).

In addition to the active ingredient and the carrier base, the compositions of the invention may contain other ingredients such as antioxidants, buffers, emulsifying agents, perfumes, preservatives and solvents which confer on the product properties desirable in a topical formulation. In particular, buffers may be employed to adjust the pH of the composition to within the range of, for example 4 to 5.5 (e.g. 4.8) to maintain the active ingredient in its free acid form. The compositions can also contain other active ingredients.

In a further aspect, the invention provides a method of treating inflammation in warm blooded non-human animals which comprises topically administering to the animal an anti-inflammatory effective amount of a compound of formula I. By "topically administering" is meant administering to the exterior skin surface. The active ingredient may be administered in the form of a composition of the present invention.

EXAMPLE 1

4-(4-Chlorophenyl)-2-(4-hydroxyphenyl)thiazole-5-acetic acid 4-(Chlorophenyl)-2-(4-methoxyphenyl)thiazole-5-acetic acid (1.26 g, 3.5 mmol) was heated to reflux in a mixture of glacial acetic acid (10 cm$^3$) and 48% hydrobromic acid (20 cm$^3$) for 4 hours. On cooling, the hydrobromide salt of the title compound crystallised (1.03 g). The crystals were collected, washed with water and ether, and dried m.p. 239°-241° (decomp).

Analysis: Found: C, 47.7; H, 3.1; N, 2.4; ionic bromine 19.2. $C_{17}H_{12}ClNO_3S.HBr$ requires C, 47.8; H, 3.1; N, 3.3; ionic bromine 18.7%.

EXAMPLE 2

4-(4-Chlorophenyl)-2-(4-hydroxyphenyl)thiazole-5-acetic acid

3-Bromo-3-(4-chlorobenzoyl)propionic acid (27 g), and 4-hydroxy-thiobenzamide (14.6 g) were heated to 80° in dimethylformamide (50 ml). The reactants were kept at this temperature for 1 hour, cooled and poured onto ice. The resulting gum solidified, and was filtered, and washed with water, to give 31.6 g of powder, m.p. 184°-194° C. (decomp.). This was recrystallised from aqueous isopropanol affording 25.4 g of the title compound, hemihydrate, m.p. 192°-194° (d).

Analysis: Found: C, 57.7; H, 3.5; N, 3.6. $C_{17}H_{12}ClNO_3S.\frac{1}{2}H_2O$ requires: C, 57.55; H, 3.7; N, 3.9%.

EXAMPLE 3

4-(4-chlorophenyl)-2-(4-hydroxyphenyl)thiazole-5-acetic acid 4-(4-Chlorophenyl)-2-(4-hydroxyphenyl)-thiazole-5-acetic acid (7.0 g, 0.016 moles) was dissolved in 0.1 N sodium hydroxide (493 ml, 0.372 moles) and cooled to 0° C. Acetic anhydride (1.5 ml, 0.016 moles) was added and the mixture left standing at room temperature for 3 hours. To the solution was added dilute hydrochloric acid and the resulting precipitate was filtered off, washed with a little water, dried and recrystallised from methylethylketone to give 2-(4-acetoxyphenyl)-4-(4-chlorophenyl)thiazole-5-acetic acid as a colourless solid (2.4 gm), m.p. 177°-180° C.

2-(4-Acetoxyphenyl)-4-(4-chlorophenyl)-thiazole-5-acetic acid is hydrolysed using 2 N sodium hydroxide to give the title compound.

EXAMPLE 4

4-(4-Chlorophenyl)-2-(4-hydroxyphenyl)thiazole-5-acetic acid

By a process analogous to Example 2, methyl-3-bromo-3-(4-chlorobenzoyl)propionate and 4-hydroxy-thiobenzamide are reacted to give methyl 4-(4-chlorophenyl)-2-(4-hydroxyphenyl)thiazole-5-acetate. This compound is hydrolysed using 2 N sodium hydroxide to give the title compound.

EXAMPLE 5

4-(4-Chlorophenyl)-2-(4-hydroxyphenyl)thiazole-5-acetic acid

3-Bromo-3-(4-chlorobenzoyl)propionate acid and an equimolar amount of 4-hydroxythio-benzamide are stirred in isopropyl alcohol solvent containing sodium carbonate to give 4-(4-chlorophenyl)-4-hydroxy-2-(4-hydroxyphenyl)-2-thiazolin-5-acetic acid. This compound is dehydrated by heating to give the title compound.

EXAMPLE 6

4-(4-Chlorophenyl)-2-(4-hydroxyphenyl)thiazole-5-acetic acid 2-(4-Acetoxyphenyl)-4-(4-chlorophenyl)-thiazole-5-acetic acid (prepared according to Example 3) is hydrolysed using 2 N sodium hydroxide to give the title compound.

EXAMPLE 7

4-(4-Chlorophenyl)-2-(4-hydroxyphenyl)thiazole-5-acetic acid

3-Bromo-3-(4-chlorobenzoyl)propionate acid and an equimolar amount of 4-hydroxythio-benzamide are stirred in isopropyl alcohol solvent containing sodium carbonate to give 4-(4-chlorophenyl)-4-hydroxy-2-(4-hydroxyphenyl)-2-thiazolin-5-acetic acid. This compound is dehydrated by heating to give the title compound.

I claim:

1. A pharmaceutical composition for topical application comprising an anti-inflammatory effective amount of 4-(4-chlorophenyl)-2-(4-hydroxyphenyl)thiazole-5-acetic acid or a pharmaceutically acceptable salt thereof and a pharmaceutically acceptable for topical application carrier.

2. A pharmaceutical composition as claimed in claim 1 which is in semi solid or aerosol form for topical application.

* * * * *

UNITED STATES PATENT OFFICE
CERTIFICATE OF CORRECTION

Patent No. 4,385,059     Dated     May 24, 1983

Inventor(s)   Richard Arthur Franklin

It is certified that error appears in the above-identified patent and that said Letters Patent are hereby corrected as shown below:

Claim 1, Column 8, lines 42 and 43, delete "and a pharmaceutically acceptable for topical application carrier" and insert --and a pharmaceutically acceptable topical carrier--.

Signed and Sealed this

Twenty-second Day of November 1983

[SEAL]

Attest:

GERALD J. MOSSINGHOFF

Attesting Officer     Commissioner of Patents and Trademarks